United States Patent [19]
Matsumoto

[11] Patent Number: 5,929,254
[45] Date of Patent: Jul. 27, 1999

[54] 1,2-DIOXETANE DERIVATIVES

[75] Inventor: Masakatsu Matsumoto, Sagamihara, Japan

[73] Assignee: Fujirebio Inc., Tokyo, Japan

[21] Appl. No.: 08/814,077

[22] Filed: Mar. 10, 1997

[30] Foreign Application Priority Data

Sep. 11, 1996 [JP] Japan .................................. 8-261146

[51] Int. Cl.[6] .................................................. C07D 305/14
[52] U.S. Cl. ........................ 549/214; 549/218; 549/332; 549/510
[58] Field of Search .................... 549/510, 214, 549/218, 332

[56] References Cited

U.S. PATENT DOCUMENTS

| | | | |
|---|---|---|---|
| 4,959,182 | 9/1990 | Schapp | 252/700 |
| 5,679,802 | 10/1997 | Bronstein et al. | 549/218 |

Primary Examiner—Ba K. Trinh
Attorney, Agent, or Firm—Oblon, Spivak, McClelland, Maier & Neustadt, P.C.

[57] ABSTRACT

A 1,2-dioxetane derivative of formula (I) for use as a chemiluminescent substrate for immunoassays:

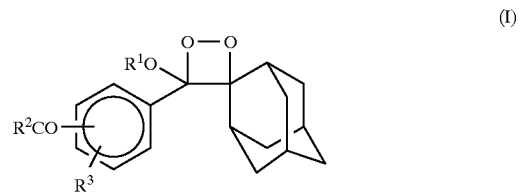

wherein $R^1$ is an alkyl group or an aryl group, $R^2$ a hydrogen atom, an alkyl group or an aryl group, and $R^3$ is a hydroxyl group, an alkoxyl group, aralkyloxy group, a phosphate salt group, or $OSi(R^4R^5R^6)$ in which $R^4$, $R^5$ and $R^6$ are each independently an alkyl group which may be the same or different.

13 Claims, No Drawings

1,2-DIOXETANE DERIVATIVES

BACKGROUND OF THE INVENTION

1. Field of the Invention

The present invention relates to 1,2-dioxetane derivatives which can be used, for instance, as chemiluminescent substrates for immunoassays.

2. Discussion of Background

Varieties of 1,2-dioxetane compounds have been conventionally synthesized. In particular, 1,2-dioxetane compounds substituted with a spiroadamantyl group at the 3 position thereof disclosed in Japanese Patent Publications 5-21918 and 5-45590, and compounds disclosed in Japanese Laid-Open Patent Applications 8-169885 are known to be useful as chemiluminescent substrates.

The above-mentioned conventional compounds exhibit high luminescence efficiencies in non-protonic solvents. However, the luminescence efficiencies thereof are extremely lowered in water or in protonic solvents. The luminescence occurs when an anion in the excited state returns to the ground state. However, the anion in water or protonic solvents returns from the excited state down to the ground state, losing its activity nonradiationally, due to various effects caused, for example, by hydrogen bonds and dipole interaction of such solvents, so that the luminescent efficiency is significantly lowered in water or protonic solvents.

Therefore even when the luminescences of such conventional compounds are applied to immunoassays in clinical examinations, since the clinical examinations are conducted in protonic solvents, luminescence with sufficient intensity for use in practice cannot always be obtained. Therefore, it is necessary to use an enhancer in order to improve the luminescence at such clinical examinations.

SUMMARY OF THE INVENTION

It is therefore an object of the present invention to provide chemiluminescent 1,2-dioxetane derivatives which exhibits high luminescence efficiency even in water or protonic solvents, without using any enhancer, and therefore, can be employed as chemiluminescent substrates for use in practice.

This object of the present invention can be achieved by a 1,2-dioxetane derivative of formula (I):

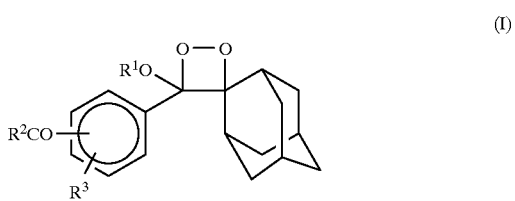

(I)

wherein $R^1$ is an alkyl group or an aryl group, $R^2$ is a hydrogen atom, an alkyl group or an aryl group, and $R^3$ is a hydroxyl group, an alkoxyl group, an aralkyloxy group, a phosphate salt group, or $OSi(R^4R^5R^6)$ in which $R^4$, $R^5$ and $R^6$ are each independently an alkyl group which may be the same or different.

DESCRIPTION OF THE PREFERRED EMBODIMENTS

The 1,2-dioxetane derivative of formula (I) of the present invention,

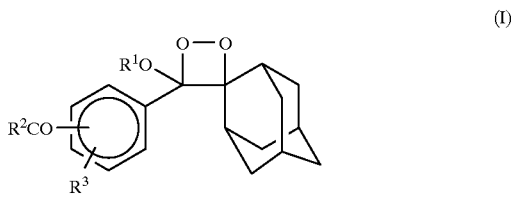

(I)

wherein $R^1$ is an alkyl or an aryl group, $R^2$ is a hydrogen atom, an alkyl group or an aryl group, and $R^3$ is a hydroxyl group, an alkoxyl group, an aralkyloxy group, a phosphate salt group, or $OSi(R^4R^5R^6)$ in which $R^4$, $R^5$ and $R^6$ are each independently an alkyl group which may be the same or different, can be synthesized in accordance with the following reaction scheme:

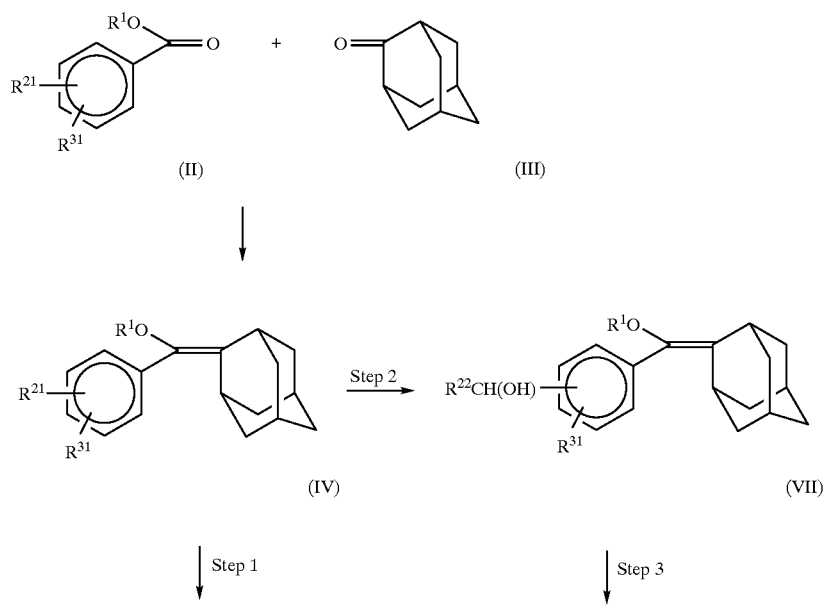

-continued (V)

(VIII)

Step 4

Step 4

(VI)

(IX)

wherein $R^1$ is the same as defined above, $R^{21}$ is a halogen atom, $R^{22}$ is an alkyl group or an aryl group, and $R^{31}$ is an alkoxyl group or an aralkyloxy group, provided that the alkoxyl group or aralkyloxy group represented by $R^{31}$ can be replaced by a group other than the alkoxyl group or aralkyloxy group prior to the above-mentioned step 4, and when $R^{31}$ is replaced by a group other than the alkoxyl group or aralkyloxy group, a 1,2-dioxetane derivative having as $R^{31}$ the replaced group can be produced.

In the description of the present invention, the term "alkyl group" means a straight chain alkyl group having 1 to 20 carbon atoms, a branched alkyl group having 3 to 20 carbon atoms, each of which may have a substituent.

Examples of the alkyl groups are methyl group, ethyl group, propyl group, butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group and icosanyl group, which may be unbranched or branched.

Examples of the substituent for the above-mentioned alkyl groups are hydroxyl group, an alkoxyl group, an aryl group and a heterocyclic group.

In the above-mentioned 1,2-dioxetane derivative of formula (I), it is preferable that the alkyl group represented by $R^1$, $R^2$, $R^4$, $R^5$ or $R^6$ be an alkyl group having 1 to 4 carbon atoms.

Examples of the alkoxyl group are methoxy group, ethoxy group, propoxy group, butoxy group, pentyloxy group, hexyloxy group, methoxyethoxy group, methoxypropoxy group, ethoxyethoxy group, ethoxypropoxy group, and methoxyethoxyethoxy group, Examples of the aryl group are phenyl group and naphthyl group.

Examples of the heterocyclic group are furyl group, thienyl group and pyridyl group.

Furthermore, in the present invention, the term "alkoxyl group" means an alkoxyl group having 1 to 20 carbon atoms, specific examples of which may be the same as mentioned above.

In the above-mentioned 1,2-dioxetane derivative of formula (I), it is preferable that the alkoxyl group represented by $R^3$ be an alkoxyl group having 1 to 4 carbon atoms.

Furthermore, in the present invention, the term "aryl group" are aromatic hydrocarbon groups such as phenyl group and naphthyl group, and heteroaryl groups which may contain nitrogen, oxygen and/or sulfur in the rings thereof.

In the present invention, the term "aralkyloxy group" means such groups as benzyloxy group, and phenethyloxy group.

Furthermore, in the present invention, the term "halogen atom" means such halogen atoms as fluorine, chlorine, and bromine.

(Step 1)

In this step, the compound of formula (V) is produced by allowing the compound of formula (IV) to react with a compound of the following formula (X) in the presence of a lithium compound. The compound of formula (IV) is obtained by subjecting the ester of formula (II) and the ketone of formula (III) to McMury reaction.

$$R^7-\underset{\underset{R^8}{|}}{N}-CHO \qquad (X)$$

wherein $R^7$ and $R^8$ are each independently an alkyl group or an aryl group.

Examples of the lithium compound for use in this step are alkyl lithiums such as methyl lithium and butyl lithium, and metal lithium.

As a solvent for use in the above reaction in this step, for example, esters such as tetrahydrofuran and diethyl ether can be employed.

It is preferable that the reaction be carried out at a temperature in the range of −80° C. to 0° C. in order to proceed the reaction efficiently.

(Step 2)

In this step, the compound of formula (VII) is produced by allowing the compound of formula (IV) to react with a compound of the following formula (XI) in the presence of a lithium compound:

$$R^4-CHO \qquad (XI)$$

wherein $R^4$ is an alkyl group or an aryl group.

Examples of the lithium compound for use in this step are alkyl lithiums such as methyl lithium and butyl lithium, and metal lithium.

As a solvent for use in the above reaction in this step, for example, ethers such as tetrahydrofuran and diethyl ether can be employed.

It is preferable that the reaction be carried out at a temperature in the range of −80° C. to 0° C. in order to proceed the reaction efficiently.

(Step 3)

In this step, the compound of formula (VIII) is produced by oxidizing the hydroxyl group in the compound of formula (VII), using an oxidizing agent.

Examples of the oxidizing agent are manganese dioxide and pyridine sulfur trioxide.

When manganese dioxide is used as the oxidizing agent in the above reaction, it is preferable that the reaction be carried out in a solvent, for examples, an aromatic hydrocarbon solvent such as benzene or toluene, a halogenated hydrocarbon solvent such as carbon tetrachloride, or hexane.

When pyridine sulfur trioxide is used as the oxidizing agent in the above reaction, dimethyl sulfoxide is preferable as the solvent for this reaction.

(Step 4)

In this step, the compound of formula (VI) or the compound of formula (IX) is produced by allowing the compound of formula (V) or the compound of formula (VIII) to react with singlet oxygen, respectively.

The reaction of the compound of formula (VI) or the compound of formula (IX) with singlet oxygen can be carried out by dissolving the compound in a solvent, for example, a halogenated hydrocarbon such as dichloromethane, dichloroethane or carbon tetrachloride, or in an alcohol such as methanol or ethanol, and irradiating the solution to visible light in the present of a photosensitizer such as Methylene Blue, Rose Bengals or tetraphenylporphine in an atomosphere of oxygen. It is preferable that this reaction be carried out at −80° C. to 0° C. in order to proceed the reaction efficiently.

A 1,2-dioxetane derivative having as $R^{31}$ a hydroxyl group can be produced by carrying out the deprotection of $R^{31}$ prior to this step. Furthermore, by introducing a phosphate salt group or a silyloxy group after the above-mentioned deprotection, a 1,2-dioxethane derivative having as $R^{31}$ the phosphate salt group or the silyloxy group can be produced.

The deprotection is carried out, using a halogenated alkali metal, such as lithium chloride or sodium chloride.

It is preferable that the reaction in this deprotection be carried out under a neutral to basic condition.

The reaction can be carried out in a non-protonic organic solvent such as dimethylformamide or dimethyl sulfoxide.

It is preferable that the reaction be carried out at a temperature in the range of 100° C. to 180° C. in order to proceed the reaction efficiently, more preferably with the solvent for the reaction mixture being refluxed, in view of the reaction operation and reactivity.

The phosphate salt group or the silyloxy group can be introduced by reacting a corresponding halogenated phosphate or a corresponding halogenated trialkylsilane with the above-mentioned deprotected 1,2-dioxetane derivative.

When chloroethylene phosphate is reacted for the introduction of the phosphoric group, the chloroethylene is converted into a sodium salt of cyanoethylphosphate by use of sodium cyanide, followed by the elimination of a cyanoethyl group, and then converted into a ammonium sodium salt. The ammonium sodium salt can be easily converted into a disodium salt by reacting with sodium hydrogencarbonate.

Other features of this invention will become apparent in the course of the following description of exemplary embodiments, which are given for illustration of the invention and are not intended to be limiting thereof.

REFERENCE EXAMPLE 1

1,1-(bicyclo[3.3.1]nonan-3,7-diyl]-2-(4-bromo-3-methoxyphenyl)-2-methoxyethene (Compound [3])

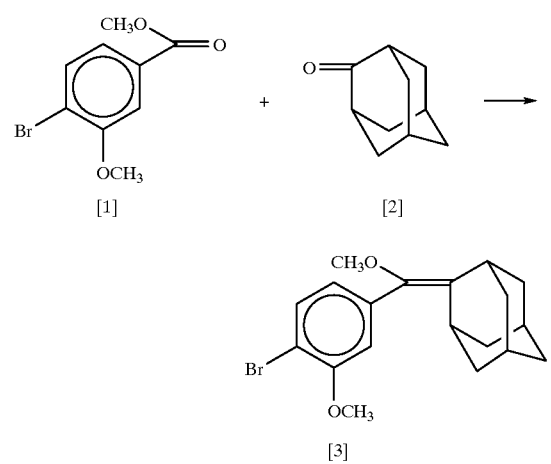

In an atmosphere of nitrogen, 4.8 g (31 mmol) of titanium trichloride was added to 80 ml of tetrahydrofuran in a 500 ml three-necked eggplant type flask equipped with a three way stop-cock, a condenser stopped with a balloon, and a 50 ml dropping funnel.

The above mixture was stirred in the atmosphere of nitrogen at room temperature for about 10 minutes.

To this mixture, 0.61 g (16.1 mmol) of lithium aluminum hydride was added under ice cooling. After the generation of hydrogen ceased, the mixture was further stirred for about 10 minutes. 2.1 ml (15 mmol) of triethylamine was then added to this reaction mixture. This mixture was further refluxed for about 15 minutes.

To this reaction mixture, under refluxing, a solution of 1.21 g (8.0 mmol) of 2-adamantanone and 990 mg (4.0 mmol) of methyl 4-bromo-3-methoxybenzoate in 25 ml of tetrahydrofuran was added dropwise over a period of 20 minutes.

The above reaction mixture was further refluxed for 3 hours and then allowed to cool to room temperature.

30 ml of distilled water was added to the reaction mixture. The mixture was extracted with 200 ml of ethyl acetate. The ethyl acetate extract layer was washed twice with 200 ml of distilled water, dried over magnesium sulfate, and then concentrated.

The residue was chromatographed on silica gel and eluted with a mixed solvent of hexane and dichloromethane (50:1), whereby 1,1-(bicyclo[3.3.1]nonan-3,7-diyl)-2-(4-bromo-3-methoxy-phenyl)-2-methoxyethene (Compound [3]) was obtained in the form of a colorless oil in a yield of 1.23 g (3.39 mmol, 84.7%).

$^1$HNMR(400 MHz, CDCl$_3$): δ1.61–2.17 (m, 12H), 2.63 (mp, 1H, α-methyne), 3.24 (mp, 1H, α-methyne), 3.30 (s, 3H, OMe), 3.89 (s, 3H, ArOMe), 6.76–7.49 (m, 3H, ArOMe), 6.76–7.49 (m, 3H, ArH) ppm IR (KRr): 2923, 2847, 1569, 1457, 1395, 1247, 1206, 1095, 1048, 1026, 866, 822, 795, 764 cm$^{-1}$

REFERENCE EXAMPLE 2

1,1-(bicyclo[3.3.1]nonan-3,7-diyl)-2-(4-formyl-3-methoxyphenyl)-2-methoxyethylene (Compound [4])

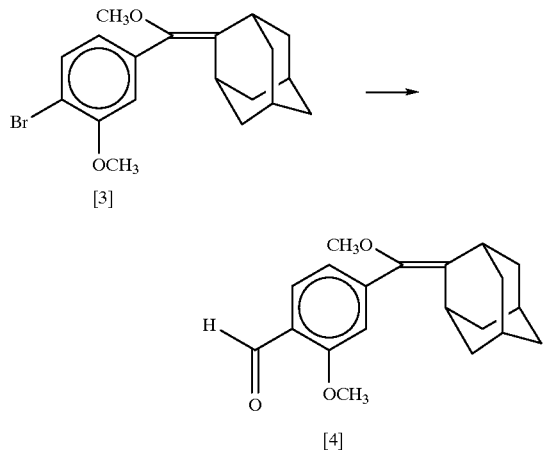

In an atmosphere of nitrogen, 1.48 g (4.08 mmol) of the compound [3] synthesized in Reference Example 1 was dissolved in 4.5 ml of tetrahydrofuran in a 25 ml eggplant type flask equipped with a tube connected to a vacuum line, and a three way stop-cock and a balloon.

The above mixture was cooled to −78° C. To this mixture, 3.3 ml of a hexane solution of n-butyl lithium (1.6M, 5.29 mmol) was added. The mixture was stirred for about 5 minutes. 0.77 ml (6.25 mmol) of N-methylformanilide was added to the mixture, and the mixture was then stirred for 90 minutes.

This reaction mixture was poured into 100 ml of a saturated aqueous solution of ammonium chloride. The mixture was then extracted with 100 ml of ethyl acetate.

The ethyl acetate extract layer was washed with 50 ml of a saturated aqueous solution of ammonium chloride, dried over magnesium sulfate, and then concentrated.

A pale yellow oil, which was obtained as the residue, was chromatographed on silica gel and eluted with a mixed solvent of hexane and ethyl acetate (15:1), whereby 1,1-(bicyclo[3.3.1]nonan-3,7-diyl)-2-(4-formyl-3-methoxyphenyl)-2-methoxyethylene (Compound [4]) was obtained in the form of white crystals in a yield of 1.08 g (3.46 mmol, 84.8%).

$^1$HNMR(400 MHz, CDCl$_3$): δ1.61–1.99 (m, 12H), 2.70 (mp, 1H, α-methyne), 3.27 (mp, 1H, α-methyne), 3.33 (s, 3H, OMe), 3.93 (s, 3H, ArOMe), 6.96–6.98 (mp, 2H, ArH), 7.78–7.81 (d, 1H, J=7.82 Hz, ArH), 10.44(s, 1H, formyl) ppm
IR (KBr): 2907, 2846, 1676, 1604, 1459, 1407, 1288, 1247, 1206, 1094, 872, 814 cm$^{-1}$
Melting Point: 92.5–94.7° C.

REFERENCE EXAMPLE 3

1,1-(bicyclo[3.3.1]nonan-3,7-diyl)-2-(4-formyl-3-hydroxyphenyl)-2-methoxyethylene (Compound [5])

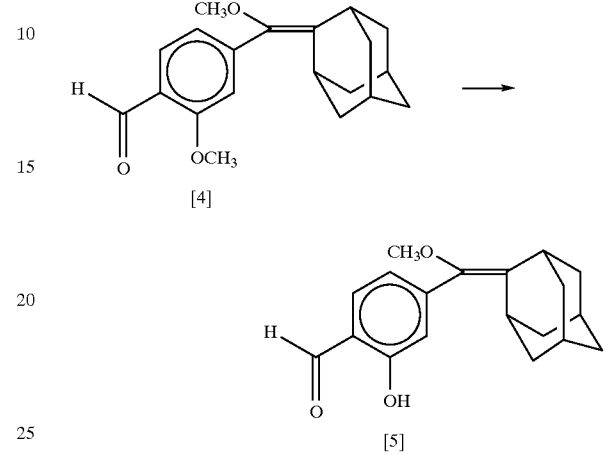

180 mg (0.58 mmol) of the compound [4] synthesized in Reference Example 2 was dissolved in 3 ml of dimethylformamide in a 10 ml two-necked eggplant type flask equipped with a three way stop-cock and a condenser.

To this solution, 147 mg (3.46 mmol) of lithium chloride was added, and the mixture was refluxed at 170° C. to 180° C. for 7 hours.

To this reaction mixture, 50 ml of a saturated aqueous solution of sodium chloride was added, and the mixture was then extracted with 50 ml of ethyl acetate.

The ethyl acetate extract layer was washed twice with 50 ml of a saturated aqueous solution of sodium chloride, dried over magnesium sulfate, and then concentrated.

The residue was chromatographed on silica gel and eluted with a mixed solvent of hexane and ethyl acetate (b 30:1), whereby 1,1-(bicyclo[3.3.1]nonan-3,7-diyl)-2-(4-formyl-3-hydroxyphenyl)-2-methoxyethylene (Compound [5]) was obtained in the form of white crystals in a yield of 136 mg (0.41 mmol, 79.0%).

$^1$HNMR(400 MHz, CDCl$_3$): δ1.76–1.98 (m, 12H, 2.72 (mp, 1H, α-methyne), 3.26 (mp, 1H, α-methyne), 3.32 (s, 3H, OMe), 6.94–7.02 (m, 2H, ArH), 7.52–7.54 (d, 1H, J=8.30 Hz, ArH), 9.87 (s, 1H, formyl), 11.06 (s, 1H, OH) ppm
IR (KBr): 2918, 2846, 1659, 1624, 1559, 1448, 1320, 1227, 1199, 1173, 1079, 936, 878, 818, 733 cm$^{-1}$
Melting Point: 89.2–90.1° C.

EXAMPLE 1

3,3-(bicyclo[3.3.1]nonan-3,7-diyl)-4-(4-formyl-3-hydroxyphenyl)-4-methoxy-1,2-dioxethane (Compound [6])

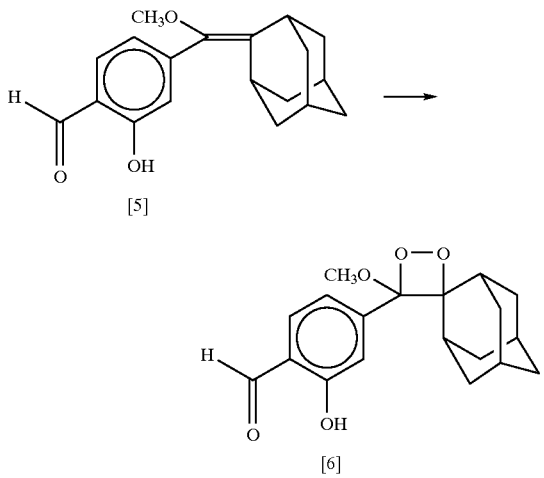

86 mg (0.29 mmol) of the compound [5] synthesized in Reference Example 3 was dissolved in 5 ml of dichloromethane. In this solution, 2 mg of tetraphenylporphine serving as a sensitizing agent was dissolved in an atmosphere of oxygen. This solution was then stirred at 0° C. for 1 hour as irradiated with a sodium lamp (940 W), and was then concentrated.

The residue was subjected to preparative TLC and eluted with a mixed solvent of hexane and ethyl acetate (10:1), whereby 3,3-(bicyclo[3.3.1]nonan-3,7-diyl)-4-(4-formyl-3-hydroxyphenyl)-4-methoxy-1,2-dioxethane (Compound [6]) was obtained in the form of white crystals in a yield of 37 mg (0.11 mmol, 38.6%).

$^1$HNMR(400 MHz, CDCl$_3$): δ1.03–1.87 (m, 12H), 2.15 (mp, 1H, α-methyne), 3.04 (mp, 1H, α-methyne), 3.23 (s, 3H, OMe), 7.26–7.66 (m, 3H, ArH), 9.96 (s, 1H, formyl), 11.05 (s, 1H, OH) ppm IR (KBr): 3650, 3629, 2447, 2917, 2858, 1662, 1289, 1101, 902, 464 cm$^{-1}$ Melting Point: >250° C.

REFERENCE EXAMPLE 4

1,1-(bicyclo[3.3.1]nonan-3,7-diyl)-2-(4-(hydroxyethyl)-3-methoxyphenyl)-2-methoxyethylene (Compound [7])

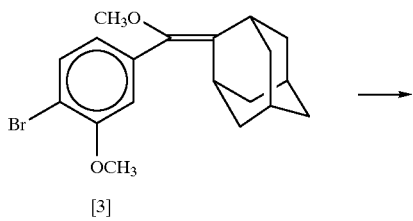

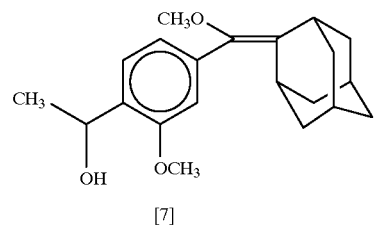

In an atmosphere of nitrogen, 286 mg of (0.79 mmol) of the compound [3] synthesized in Reference Example 1 was dissolved in 2.5 ml of tetrahydrofuran in a 10 ml eggplant type flask equipped with a tube connected to a vacuum line, a three way stop-cock and a balloon.

The above mixture was cooled to −78° C., and 0.59 ml of a hexane solution of n-butyl lithium (1.6M, 0.95 mmol) was added thereto. The mixture was stirred for about 10 minutes. To this mixture, acetaldehyde was added in large excess. The mixture was further stirred for 1 hour.

To the above mixture, 100 ml of a saturated aqueous solution of ammonium chloride was added, and the mixture was extracted with 80 ml of ethyl acetate.

The ethyl acetate extract layer was washed twice with 50 ml of a saturated aqueous solution of ammonium chloride, dried over magnesium sulfate, and then concentrated.

A pale yellow oil, which was obtained as the residue, was chromatographed on silica gel and eluted with a mixed solvent of hexane and ethyl acetate (10:1), whereby 1,1-(bicyclo[3.3.1]nonan-3,7-diyl)-2-(4-(1-hydroxyethyl)-3-methoxyphenyl)-2-methoxyethylene (Compound [7]) was obtained in the form of a colorless oil in a yield of 108 mg (0.34 mmol, 42.7%).

$^1$HNMR(400 MHz, CDCl$_3$): δ1.52–1.54 (d, 3H, J=6.83 Hz, Me), 1.75–1.98 (m, 12H), 2.66 (mp, 1H, α-methyne), 2.71–2.72 (d, 1H, J=4.88 Hz, OH), 3.25 (mp, 1H, α-methyne), 3.30 (s, 3H, OMe), 3.86 (s, 3H, ArOMe), 5.06–5.11 (pent, 1H, J=6.02 Hz, methyne), 6,.87–6.90 (m, 2H, ArH), 7.26–7.29 (m, 1H, ArH) ppm IR (KBr): 3420, 2906, 2846, 1654, 1608, 1570, 1498, 1458, 1404, 1241, 1205, 1165, 1080, 866, 835, 796 cm$^{-1}$

REFERENCE EXAMPLE 5

2-(4-acetyl-3-methoxyphenyl)-1,1-(bicyclo[3.3.1]nonan-3,7-diyl)-2-methoxyethylene (Compound [8])

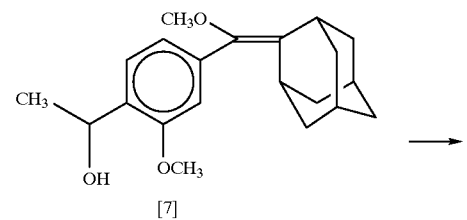

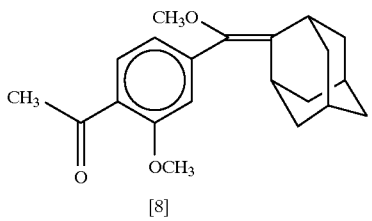

[8]

108 mg (0.34 mmol) of the compound [7] synthesized in Reference Example 4 was dissolved in 5 ml of benzene in a 50 ml eggplant type flask.

To this solution, 1.03 mg (11.85 mmol) of manganese dioxide was added, and the mixture was stirred at room temperature for 6 hours.

After the progress of the reaction was confirmed, using TLC, the manganese dioxide was filtered off through celite, and the filtrate was concentrated.

The residue was chromatographed on silica gel and eluted with a mixed solvent of hexane and ethyl acetate (5:1), whereby 2-(4-acetyl-3-methoxyphenyl)-1,1-(bicyclo[3.3.1]nonan-3,7-diyl)-2-methoxyethylene (Compound [8]) was obtained in the form of white crystals in a yield of 65 mg (0.20 mmol, 59.0%).

$^1$HNMR(400 MHz, CDCl$_3$): δ1.77–1.98 (m, 12H), 2.63 (s, 3H, AcMe), 2.69 (mp, 1H, α-methyne), 3.26 (mp, 1H, α-methyne), 3.32 (s, 3H, OMe), 3.91 (s, 3H, ArOMe), 6.92–6.95 (m, 2H, ArH), 7.71–7.73 (d, 1H, J=7.82 Hz, ArH) ppm IR (KBr): 3448, 2906, 2845, 1671, 1600, 1404, 1292, 1241, 1207, 1178, 1097 cm$^{-1}$ Melting Point: 83.5–84.2° C.

REFERENCE EXAMPLE 6

2-(4-acetyl-3-hydroxyphenyl)-1,1-(bicyclo[3.3.1]nonan-3,7-diyl)-2-methoxyethylene (Compound [9])

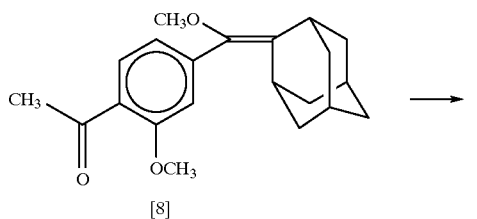

240 mg (0.74 mmol) of the compound [8] synthesized in Reference Example 5 was dissolved in 5 ml of dimethylformamide in a 10 ml two-necked eggplant type flask equipped with a three way stop-cock and a condenser.

To this solution, 231 mg (5.45 mmol) of lithium chloride was added, and the mixture was refluxed at 170° C. to 180° C. for 20 hours.

To this mixture, 100 ml of a saturated aqueous solution of ammonium chloride was added, and the mixture was extracted with 100 ml of ethyl acetate.

The ethyl acetate extract layer was washed twice with 50 ml of a saturated aqueous solution of ammonium chloride, dried over magnesium sulfate, and then concentrated.

The residue was chromatographed on silica gel and eluted with a mixed solvent of hexane, dichloromethane and ether (10:1:1), whereby 2-(4-acetyl-3-hydroxyphenyl)-1,1-(bicyclo[3.3.1]nonan-3,7-diyl)-2-methoxyethylene (Compound [9]) was obtained in the form of pale yellow crystals in a yield of 186 mg (0.60 mmol, 81.2%).

$^1$HNMR(400 MHz, CDCl$_3$): δ1.76–1.99 (m, 12H), 2.64 (s, 3H, acetyl, 2.67 (mp, 1H, α-methyne), 3.25 (mp, 1H, α-methyne), 3.32 (s, 3H, OMe), 6.89–6.93 (m, 2H, ArH), 7.71–7.73 (d, 1H, J=8.30 Hz, ArH), 11.05 (s, 1H, OH) ppm IR (KBr): 3448, 2915, 2847, 1638, 1560, 1374, 1322, 1228, 1210, 1097, 1079, 794 cm$^{-1}$ Melting Point 82.1–83.5° C.

EXAMPLE 2

4-(4-acetyl-3-hydroxyphenyl)-3,3-(bicyclo[3.3.1]nonan-3,7-diyl)-4-methoxy-1,2-dioxethane (Compound [10])

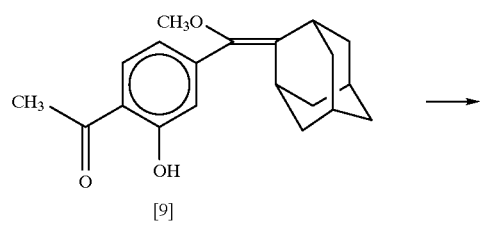

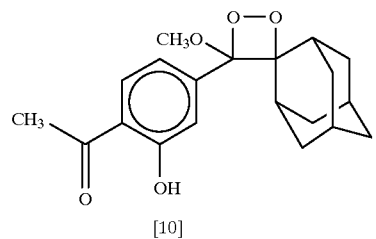

[10]

136 mg (0.44 mmol) of the compound [9] synthesized in Reference Example 6 was dissolved in 8 ml of dichloromethane. In this solution, 3 mg of tetraphenylporphine serving as a sensitizing agent was further dissolved in an atmosphere of oxygen.

This solution was stirred at −78° C. for 90 minutes as irradiated with a sodium lamp (940 W).

This reaction mixture was concentrated, and then recrystallized from a mixed solvent of ethyl acetate and methanol, whereby 4-(4-acetyl-3-hydroxyphenyl)-3,3-(bicyclo[3.3.1]nonan-3,7-diyl)-4-methoxy-1,2-dioxetane (Compound [10]) was obtained in the form of white crystals in a yield of 125.3 mg (0.36 mmol, 83.4%).

$^1$HNMR(400 MHz, CDCl$_3$): δ1.05–1.89 (m, 12H), 2.18 (mp, 1H, α-methyne), 2.68 (s, 3H, acetyl), 3.03 (mp, 1H, α-methyne), 3.23 (s, 3H, OMe), 7.16–7.82 (m, 3H, ArH), 12.28 (s, 1H, OH) ppm IR (KBr): 3448, 2919, 2860, 1648, 1371, 1321, 1299, 1176, 1097, 1070, 1011, 954 cm$^{-1}$ Mass (m/z, %): 344 (M$^+$, trace), 312 (24), 278 (4), 194 (60), 179 (100)

Melting Point: 104.2–106.1° C.

REFERENCE EXAMPLE 7

1,1-(bicyclo[3.3.1]nonan-3,7-diyl)-2-(4-(1-hydroxybenzyl)-3-methoxyphenyl)-2-methoxyethylene (Compound [11])

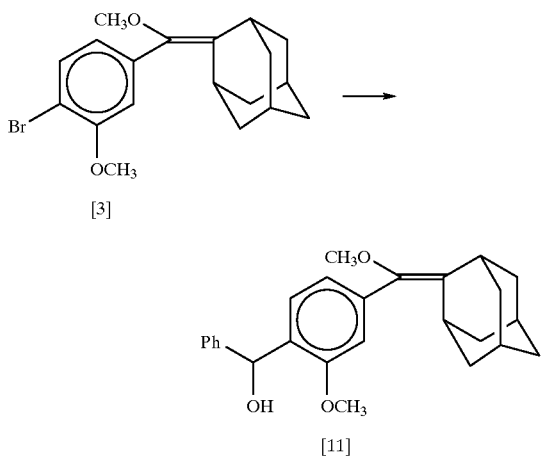

In an atmosphere of nitrogen, 1.52 g (4.19 mmol) of the compound [3] synthesized in Reference Example 1 was dissolved in 4.5 ml of tetrahydrofuran in a 25 ml eggplant type flask equipped with a tube connected to a vacuum line, a three way stop-cock and a balloon.

This mixture was cooled to −78° C., and 3.30 ml (5.29 mmol) of a hexane solution of n-butyl lithium (1.6M) was added thereto. The mixture was stirred for about 5 minutes, and 0.73 ml (6.61 mmol) of benzaldehyde was added thereto. The mixture was further stirred for 90 minutes.

This reaction mixture was then poured into 100 ml of a saturated aqueous solution of ammonium chloride, and the mixture was then extracted with 100 ml of ethyl acetate.

The ethyl acetate extract layer was washed twice with 50 ml of a saturated aqueous solution of ammonium chloride, dried over magnesium sulfate, and then concentrated.

A pale yellow oil, which was obtained as the residue, was chromatographed on silica gel and eluted with a mixed solvent of hexane and ethyl acetate (15:1), whereby 1,1-(bicyclo[3.3.1]nonan-3,8-diyl)-2-(4-(1-hydroxybenzyl)-3-methoxyphenyl)-2-methoxyethylene (Compound [11]) was obtained in the form of white crystals in a yield of 1.38 g (3.69 mmol, 88.1%).

$^1$HNMR(400 MHz, CDCl$_2$): δ1.77–1.97 (m, 12H), 2.65 (mp, 1H, α-methyne), 3.02–3.03 (d, 1H, J=5.37 Hz, OH), 3.25 (mp, 1H, α-methyne), 3.30 (s, 3H, OMe), 3.83 (s, 3H, ArOMe), 6.06–6.08 (d, 1H, J=4.88 Hz, methyne), 6.87–7.44 (m, 8H, ArH) ppm
IR (KBr): 3444, 2923, 1607, 1570, 1496, 1457, 1403, 1244, 1094, 1094, 1041, 874, 735, 699 cm$^{-1}$

REFERENCE EXAMPLE 8

4-[2,2-(bicyclo[3.3.1]nonan-3,7-diyl)-1-methoxyethenyl]-2-methoxybenzophenone (Compound [12])

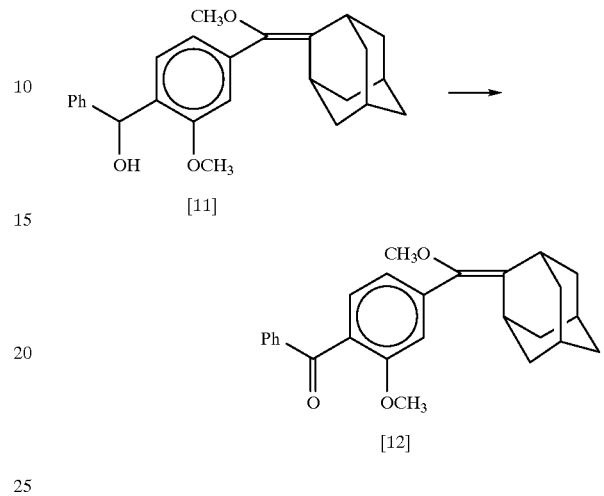

1.24 g (3.32 mmol) of the compound [11] synthesized in Reference Example 7 was dissolved in 12 ml of hexane in a 50 ml eggplant type flask.

To this solution, 13.67 g (0.157 mmol) of manganese dioxide was added, and the mixture was stirred at room temperature for 26 hours.

The manganese dioxide was filtered off through celite, and the filtrate was concentrated.

The residue was chromatographed on silica gel and eluted with a mixed solvent of hexane and ethyl acetate (15:1), whereby 4-[2,2-(bicyclo[3.3.1]nonan-3,7-diyl)-1-methoxyethenyl]-2-methoxybenzophenone (Compound [12]) was obtained in the form of a pale yellow oil in a yield of 1.06 g (2.85 mmol, 85.8%).

$^1$HNMR(400 MHz, CDCl$_3$): δ1.80–2.05 (m, 12H), 2.75 (mp, 1H, α-methyne), 3.29 (mp, 1H, α-methyne), 3.36 (s, 3H, OMe), 3.73 (s, 3H, ArOMe), 6.97–7.86 (m, 7H, ArH) ppm
IR (KBr): 3448, 2910, 2847, 1659, 1604, 1560, 1450, 1401, 1319, 1288, 1244, 1205, 1151, 1092, 1079, 1036, 930, 868, 715 cm$^{-1}$
Melting Point:

REFERENCE EXAMPLE 9

4-[2,2-(bicyclo[3.3.1]nonan-3,7-diyl)-1-methoxyethenyl]-2-hydroxybenzophenone (Compound [13])

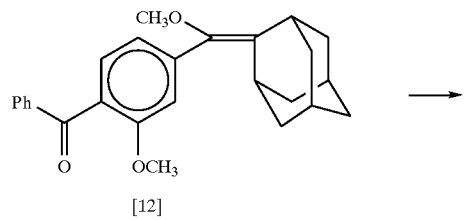

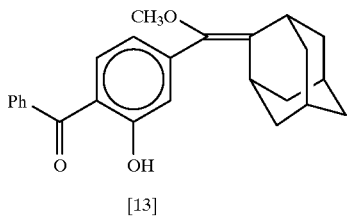

[13]

986 mg (2.66 mmol) of the compound [12] synthesized in Reference Example 8 was dissolved in 10 ml of dimethylformamide in a 30 ml two-necked eggplant type flask equipped with a three way stop-cock and a condenser.

To this solution, 699 mg (16.49 mmol) of lithium chloride was added, and the mixture was refluxed at 170° C. to 180° C. for 23 hours.

To this reaction mixture, 100 ml of a saturated aqueous solution of ammonium chloride was added, and the mixture was extracted with 100 ml of ethyl acetate.

The ethyl acetate extract layer was washed twice with 50 ml of a saturated aqueous solution of ammonium chloride, dried over magnesium sulfate, and then concentrated.

The residue was chromatographed on silica gel and eluted with a mixed solvent of hexane and ethyl acetate (20:1), whereby 4-[2,2-(bicyclo[3.3.1]nonan-3,7-diyl)-1-methoxyethenyl]-2-hydroxybenzophenone (Compound [13]) was obtained in the form of white crystals in a yield of 786 mg (2.15 mmol, 80.9%).

$^1$HNMR(400 MHz, CDCl$_3$): δ1.83–1.99 (m, 12H, 2.78 (mp, 1H, α-methyne), 3.26 (mp, 1H, α-methyne), 3.35 (s, 3H, OMe), 6.85–7.741 (m, 8H, ArH), 12.16 (s, 1H, OH) ppm
IR (KBr): 3447, 2918, 2846, 1625, 1607, 1574, 1559, 1446, 1335, 1285, 1267, 1239, 1088, 945, 705 cm$^{-1}$
Melting Point: 87.2–87.7° C.

EXAMPLE 3

4-[4,4-(bicyclo[3.3.1]nonan-3,7-diyl)-3-methoxy-1,2-dioxetane-3-yl]-2-hydroxybenzophenone (Compound [14])

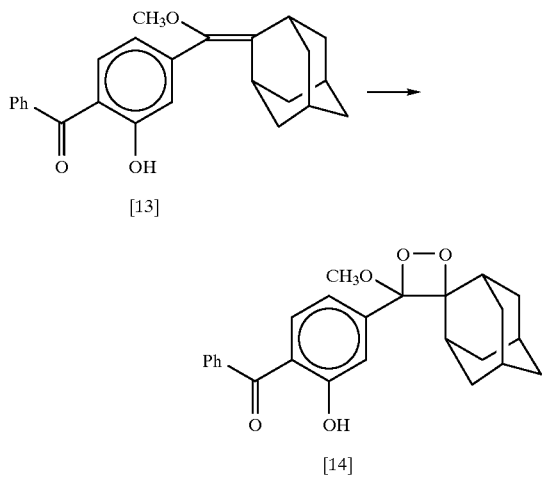

97 mg (0.27 mmol) of the compound [13] synthesized in Reference Example 9 was dissolved in 3 ml of dichloromethane. In this solution, 1.5 mg of tetraphenylporphine serving as a sensitizing agent was further dissolved in an atmosphere of oxygen.

This solution was stirred at −78° C. for 1 hour as irradiated with a sodium lamp (940 W).

This reaction mixture was concentrated and then subjected to preparative TLC and eluted with a mixed solvent of hexane and dichloromethane (5:8), whereby 4-[4,4-(bicyclo[3.3.1]nonan-3,7-diyl)-3-methoxy-1,2-dioxetane-3-yl]-2-hydroxybenzophenone (Compound [14]) was obtained in the form of a pale yellow oil in a yield of 59 mg (0.15 mmol, 54.2%).

$^1$HNMR(400 MHz, CDCl$_3$): δ1.10–1.91 (m, 12H), 2.21 (mp, 1H, α-methyne), 3.04 (mp, 1H, α-methyne), 3.25 (s, 3H, OMe), about 7.00–7.71 (brm, 3H, ArH), 12.01 (s, 1H, OH) ppm
IR (KBr): 3448, 2917, 2857, 1631, 1577, 1334, 1330, 1268, 1245, 1206, 1175, 1092, 1071, 942, 926, 709 cm$^{-1}$

TEST EXAMPLE 1

1 ml of a 2.94×10$^{+1}$M dimethylsulfoxide(DMSO) solution of 4-(4-acetyl-3-hydroxyphenyl)-3,3-(bicyclo[3.3.1]nonan-3,7-diyl)-4-methoxy-1,2-dioxethane (Compound [10]) synthesized in Example 2 was added to 2 ml of 1.5×10$^{-1}$M DMSO solution of tetrabutylammonium fluoride at 25° C.

The luminescence at the moment of the addition of the compound [10] to the DMSO solution of tetrabutylammonium fluoride was measured with a fluorescence analyzer. The results are shown in TABLE 1.

TEST EXAMPLE 2

1 ml of a 3.12×10$^{-3}$M methanol solution of 4-(4-acetyl-3-hydroxyphenyl)-3,3-(bicyclo[3.3.1]nonan-3,7-diyl)-4-methoxy-1,2-dioxethane (Compound [10]) synthesized in Example 2 was added to 2 ml of a 1.5×10$^{-1}$M methanol solution of cesium hydroxide at 25° C.

The luminescence at the moment of the addition of the compound [10] to the methanol solution of cesium hydroxide was measured with a fluorescence analyzer in the same manner as in Test Example 1. The results are shown in TABLE 1.

TEST EXAMPLE 3

The measurement of the luminescence of the compound [10] in Test Example 2 was repeated in the same manner as in Test Example 2 except that the methanol used as the solvent for cesium hydroxide employed in Test Example 2 was replaced by an aqueous solution of methanol (water: 50%) without changing the concentration of cesium in the diluted methanol solution.

Thus, the luminescence at the moment of the addition of the compound [10] to the diluted methanol solution of cesium hydroxide was measured with a fluorescence analyzer in the same manner as in Test Example 1. The results are shown in TABLE 1.

TEST EXAMPLE 4

The measurement of the luminescence of the compound [10] in Test Example 2 was repeated in the same manner as in Test Example 2 except that the methanol used as the solvent for cesium hydroxide employed in Test Example 2 was replaced by an aqueous solution of methanol (water: 97%) without changing the concentration of cesium in the diluted methanol solution.

Thus, the luminescence at the moment of the addition of the compound [10] to the diluted methanol solution of cesium hydroxide was measured with a fluorescence analyzer in the same manner as in Test Example 1. The results are shown in TABLE 1.

TABLE 1

Luminescence Characteristics of 4-(4-acetyl-3-hydroxyphenyl)-3,3-(bicyclo[3.3.1]nonane-3,7-diyl)-4-methoxy-1,2-dioxetane (Compound [10])

| Solvent | Luminescence Quantum Efficiency | Half-life (sec) of Luminescence | λmax (nm) |
|---|---|---|---|
| DMSO | 0.13 | $2.3 \times 10^4$ | 486 |
| Methanol | 0.030 | $1.2 \times 10^5$ | 493 |
| Aqueous solution of methanol (water: 50%) | 0.023 | $2.9 \times 10^4$ | 496 |
| Aqueous solution of methanol (water: 97%) | 0.0064 | $8.2 \times 10^3$ | 496 |

COMPARATIVE TEST EXAMPLE 1

1 ml of a $2.94 \times 10^{-3}$M dimethylsulfoxide (DMSO) solution of 3,3-(bicyclo[3.3.1]nonan-3,7-diyl)-4-(3-hydroxyphenyl)-4-methoxy-1,2-dioxetane (Comparative Compound) was added to 2 ml of $1.5 \times 10^{-1}$M DMSO solution of tetrabutylammonium fluoride at 25° C.

The luminescence at the moment of the addition of the comparative compound to the DMSO solution of tetrabutylammonium fluoride was measured with a fluorescence analyzer in the same manner as in Example 1. The results are shown in TABLE 2.

COMPARATIVE TEST EXAMPLE 2

1 ml of a $3.12 \times 10^{-3}$M methanol solution of 3,3-(bicyclo[3.3.1]nonan-3,7-diyl)-4-(3-hydroxyphenyl)-4-methoxy-1,2-dioxetane (Comparative Compound) was added to 2 ml of a $1.5 \times 10^{-1}$M methanol solution of cesium hydroxide at 25° C.

It was tried to measure the luminescence at the moment of the addition of the comparative compound to the methanol solution of cesium hydroxide with a fluorescence analyzer in the same manner as in Test Example 1. However, the intensity of the luminescence was extremely small and the half-life of the luminescence was extremely long, so that it was impossible to measure the luminescence quantum efficiency, the half-life (sec) of the luminescence and λmax (nm).

COMPARATIVE TEST EXAMPLE 3

The measurement of he luminescence of the comparative compound in Comparative Test Example 2 was repeated in the same manner as in Comparative Test Example 2 except that the methanol used as the solvent for cesium hydroxide employed in Comparative Test Example 2 was replaced by an aqueous solution of methanol (water: 50%) without changing the concentration of cesium in the diluted methanol solution.

Thus, the luminescence at the moment of the addition of the comparative compound to the diluted methanol solution of cesium hydroxide was measured with a fluorescence analyzer in the same manner as in Test Example 1. The results are shown in TABLE 2.

COMPARATIVE TEST EXAMPLE 4

The measurement of the luminescence of the comparative compound in Comparative Test Example 2 was repeated in the same manner as in Comparative Test Example 2 except that the methanol used as the solvent for cesium hydroxide employed in Comparative Test Example 2 was replaced by an aqueous solution of methanol (water: 97%) without changing the concentration of cesium in the diluted methanol solution.

Thus, the luminescence at the moment of the addition of the comparative compound to the diluted methanol solution of cesium hydroxide was measured with a fluorescence analyzer in the same manner as in Test Example 1. The results are shown in TABLE 2.

TABLE 2

Luminescence Characteristics of 3,3-(bicyclo[3.3.1]nonane-3,7-diyl)-4-(3-hydroxyphenyl)-4-methoxy-1,2-dioxetane (Comparative Compound)

| Solvent | Luminescence Quantum Efficiency | Half-life (sec) of Luminescence | λmax (nm) |
|---|---|---|---|
| DMSO | 0.22 | 5.1 | 465 |
| Aqueous solution of methanol (water: 50%) | $3.9 \times 10^{-5}$ | 452 | 472 |
| Aqueous solution of methanol (water: 97%) | $6.7 \times 10^{-6}$ | 173 | 474 |

According to the resent invention, 1,2-dioxetane derivatives which exhibit stable and high luminescence quantum efficiencies even in water and protonic solvents, without using any enhancer.

What is claimed is:

1. A 1,2-dioxetane derivative of formula (I):

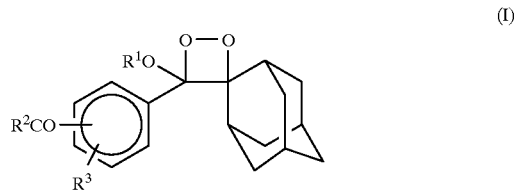

(I)

wherein $R^1$ is an alkyl group or an aryl group, $R^2$ is a hydrogen atom, an alkyl group or an aryl group, and $R^3$ is a hydroxyl group, an alkoxyl group, aralkyloxy group, a phosphate salt group, or OSi ($R^4R^5R^6$) in which $R^4$, $R^5$, and $R^6$ are each independently an alkyl group which may be the same or different, wherein $R^1$–$R^6$ are selected such that said 1,2-dioxetane derivative exhibits readily detectable luminescence in a protonic solvent, in the absence of an enhancing agent.

2. A 1,2-dioxetane derivative of formula (II):

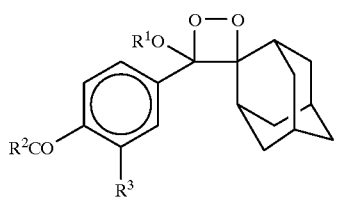

(II)

wherein $R^1$ is an alkyl group or an aryl group, $R^2$ is a hydrogen atom, an alkyl group or an aryl group, and $R^3$ is a hydroxyl group, an alkoxyl group, aralkyloxy group, a phosphate salt group, or OSi ($R^4R^5R^6$) in which $R^4R^5$, and $R^6$ are each independently an alkyl group which may be the same or different, wherein $R^1$–$R^6$ are selected such that said 1,2-dioxetane derivative exhibits readily detectable luminescence in a protonic solvent, in the absence of an enhancing agent.

3. The 1,2-dioxetane derivative as claimed in claim 2, wherein $R^1$ and $R^2$ in formula (II) are each independently an alkyl group which may be the same or different.

4. The 1,2-dioxetane derivative as claimed in claim 3, wherein $R^1$ and $R^2$ in formula (II) are each independently an alkyl group having 1 to 4 carbon atoms.

5. The 1,2-dioxetane derivative as claimed in claim 4, wherein $R^3$ in formula (II) is a hydroxyl group.

6. The 1,2-dioxetane derivative as claimed in claim 4, wherein $R^3$ in formula (II) is a phosphate salt group.

7. The 1,2-dioxetane derivative as claimed in claim 4, wherein $R^3$ in formula (II) is OSi($R^4R^5R^6$) in which $R^4$, $R^5$ and $R^6$ are each independently an alkyl group which may be the same or different.

8. The 1,2-dioxetane derivative as claimed in claim 7, wherein $R^4$, $R^5$ and $R^6$ are each independently an alkyl group having 1 to 4 carbon atoms.

9. The 1,2-dioxetane derivative as claimed in claim 4, wherein $R^3$ in formula (II) is an alkoxyl group.

10. The 1,2-dioxetane derivative as claimed in claim 9, wherein said alkoxy group represented by $R^3$ is an alkoxyl group having 1 to 4 carbon atoms.

11. The 1,2-dioxetane derivative of claim 1, wherein said 1,2-dioxetane derivative exhibits a luminescence quantum efficiency in a solvent comprised of water and methanol, with water being present in an amount of 97%, by volume, of at least 0.0064.

12. The 1,2-dioxetane derivative of claim 1, wherein said group $R^2$ is $CH_3$.

13. A method of using a 1,2-dioxetane derivative as recited in claim 1, comprising adding said dioxetane derivative to a preparation comprising a protonic solvent in the absence of any luminescence enhancing agents, and observing said preparation to determine whether any luminescence is observed, wherein observed luminescence is indicative of the presence, in said preparation, of an agent which causes said 1,2-dioxetane derivative to luminescence.

* * * * *